United States Patent [19]

Johnson et al.

[11] Patent Number: 5,149,697
[45] Date of Patent: Sep. 22, 1992

[54] COBALT PORPHYRIN PHARMACEUTICAL COMPOSITIONS

[75] Inventors: Michael R. Johnson, Chapel Hill; Stephen V. Frye, Durham, both of N.C.

[73] Assignee: Glaxo Inc., Research Triangle Park, N.C.

[21] Appl. No.: 687,268

[22] Filed: Apr. 18, 1991

[51] Int. Cl.$^5$ .................. A61K 31/555; C07D 487/22
[52] U.S. Cl. ..................................... 514/185; 540/145
[58] Field of Search ......................... 540/145; 514/185

[56] References Cited

U.S. PATENT DOCUMENTS

| | | | |
|---|---|---|---|
| 4,393,071 | 7/1983 | Fujii et al. | 424/274 |
| 4,619,923 | 10/1986 | Kappas et al. | 514/185 |
| 4,657,902 | 4/1987 | Kappas et al. | 514/185 |
| 4,782,049 | 11/1988 | Kappas et al. | 514/185 |
| 4,948,792 | 8/1990 | Kappas et al. | 514/185 |
| 4,961,920 | 10/1990 | Ward et al. | 424/9 |

FOREIGN PATENT DOCUMENTS

| | | |
|---|---|---|
| 8704927 | 8/1987 | World Int. Prop. O. |
| 9009173 | 8/1990 | World Int. Prop. O. |

OTHER PUBLICATIONS

Galbraith et al. Proc. Natl. Acad. Sci. USA vol. 86, 7653-7657, (1989).
Galbraith et al. Pharmacology 34:241-249 (1987).
Galbraith et al. Neuroendocrinology, 49:641-648 (1989).
Galbraith et al. Biochemical and Biophysical Research Communication, vol. 145, No. 1, 376-383 (1987).
Drummond et al. Proc. Natl. Acad. Sci. USA vol. 79, pp. 2384-2388 (1982).
Smith et al. Pharmacology 34:9-16 (1980).
Galbraith et al. J. Steroid Biochem, Mar. (1989).
Hambright, Inorg. Nucl. Chem. Letters vol. 1, pp. 217-222, 1976.
Jones et al. Biochemical and Biophysical Research Communications, vol. 41, No. 4, 1970.
Jones et al. Biochem. J. (1969) 113, 507.

*Primary Examiner*—Cecilia Tsang
*Assistant Examiner*—Jyothsra Venkat
*Attorney, Agent, or Firm*—Charles T. Joyner; David J. Levy

[57] ABSTRACT

Pharmaceutical compositions containing cobalt porphyrins of the following formula (I):

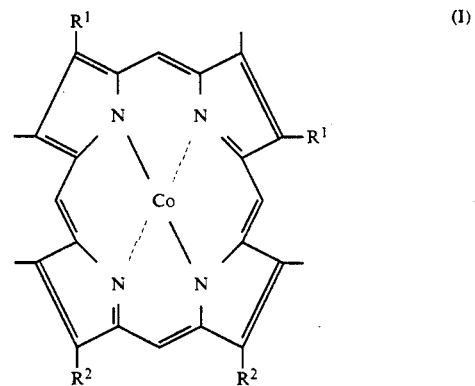

wherein $R^1 = -CH_2CH_2CN$ and $R^2 = -CH_2CH_2COOH$ or $R^1$ and $R^2 = -CH_2CH_2COOH$ or $R^1 = -H$ and $R^2 = -CH_2CH_2COOH$ or a salt or ligand complex thereof and their use in controlling obesity.

9 Claims, No Drawings

COBALT PORPHYRIN PHARMACEUTICAL COMPOSITIONS

BACKGROUND OF THE INVENTION

Cobalt prophyrins are known to have various endocrine activities including the regulation of food intake for controlling obesity. Publications include those of R. A. Galbraith et al. in Proc. Natl. Acad. Sci. U.S.A., Vol 86, pp. 7653–7657 (1989); in Pharmacology 34:241–249 (1987); in Neuroendocrinology 1989, 49: 641–648; in Biochemical and Biophysical Research Communications, Vol 145, No. 1, p. 376–383 (1987); and those of George S. Drummond et al. in Proc. Natl. Acad. Sci. U.S.A. Vol. 79, pp. 2384–2388, April 1982; and Terry J. Smith in Pharmacology, Vol. 34:9, pp. 9–16 (1986).

Phototherapeutic porphyrin-type dimers are disclosed in U.S. Pat. No. 4,961,920. Various porphyrins are disclosed in U.S. Pat. No. 4,393,071 to be useful in treating tumors; in U.S. Pat. No. 4,619,923 to control trytophan metabolism; in U.S. Pat. No. 4,657,902 to inhibit heme metabolism; and in U.S. Pat. No. 4,782,049 to treat psoriasis. Methods for suppressing the endocrine system with cobalt protoporphyrin are described in U.S. Pat. No. 4,948,792, PCT Patent No. WO 87/04927 and for weight loss in PCT Patent No. WO 90/09173. The adjustment of testosterone levels in rats after the administration of cobalt protoporphyrin is taught by Galbraith et al in J. Steroid Biochem 32(3) p. 421–427 (March 1989).

Several compounds used in the invention or compounds related thereto are set forth by P. Hambright et al in Inorganic Nuclear Chemistry Letters, Vol. 12, pp. 217–222 (1976) and by M. S. Jones et al in Biochemical and Biophysical Research Communications, Vol. 41, 1970, pp. 1072–1079 and in Biochem. Journal, 1969, Vol. 113, pp. 507–514.

SUMMARY OF THE INVENTION

The invention comprises pharmaceutical compositions of cobalt porphyrins having the following formula (I):

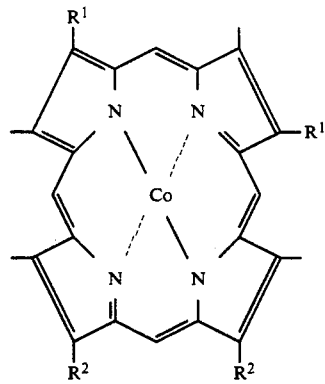

or a salt or complex thereof with a ligand wherein the cobalt atom is in the +2 or +3 oxidation state, wherein:
$R^1$ is —$CH_2CH_2CN$ and $R^2$ is —$CH_2CH_2COOH$; or
$R^1$ is —$CH_2CH_2COOH$ and $R^2$ is —$CH_2CH_2COOH$; or
$R^1$ is hydrogen and $R^2$ is —$CH_2CH_2COOH$.

Also included are methods of use with such pharmaceutical compositions including the treatment of obesity.

DETAILED DESCRIPTION OF THE INVENTION

The ligands which may attach to the cobalt atom of (I) include aromatic bases such as pyridine, imidazole or 2-methylimidazole in amounts which may be up to 2 equivalents. As a salt of (I), anions may be chloride, bromide, carboxylate or hydroxide. Cations, e.g. when a —COOH is present in $R^1$ or $R^2$ are alkali metals such as Na and K.

Particular compounds of formula (I) include the following:

2,4-Bis(2-cyanoethyl)-6,7-Bis(2-carboxyethyl)-1,3,5,8-tetramethyl cobalt porphyrin; or
Cobalt Coproporphyrin III; or
Cobalt Deuteroporphyrin IX,
or a salt complex thereof with a ligand.

SYNTHESIS SCHEMES

Synthetic pathways for the compounds of formula (I) are set forth in the following Examples with individual steps being the same or analogous to steps taught in the art, such as the text "Porphyrins and Metalloporphyrins" Ed. by K. M. Smith, Elsevier Scientific Pub. Co (1975) (ISBN 0-444-41375-8).

PHARMACOLOGY

Measurement of the effects of cobalt porphyrins on food intake, body weight and serum hormone concentrations can be carried out according to the following protocol:

Male Long-Evans rats (Charles River, Raleigh, N.C.), weighing between 250–325 grams, were used to measure the effects of subcutaneous (s.c.) administration of CoMP (cobalt mesoporphyrin), control (0.5% methylcellulose or 0.9% NaCl, 2 ml/kg) and the porphyrins of the invention on food intake, body weight (B.W.) and serum concentrations of $T_3$, $T_4$ and testosterone. The analogues were measured in one of four test groups. Each test group always contained a group receiving 50 mm/kg CoMP as well as a control group. All cobalt porphyrins were ground with a mortar and pestle, weighed, suspended in 0.5% methylcellulose, and administered s.c. at 50 mm/kg B.W. Solid food (Lab Blox, Purina Rodent Laboratory Chow #5001) intake (to the nearest 0.1 g) and B.W. (to the nearest g) were measured before drug administration and on days 1, 3, 7, 14 and 21 following drug administration, and compared with values from appropriate control-treated rats with the 2-tailed t-test for independent samples. Either on day 3 or day 22 following drug administration rats were guillotined, their blood was collected and centrifuged, and collected serum was frozen in triplicate at −70° C. Subsequently, serum samples were assayed for $T_3$, $T_4$ or testosterone by radioimmunoassay, and values of test compound groups were compared with appropriate control groups with the 2-tailed t-test for independent samples.

The methods of the invention are useful for the treatment of diabetes mellitus, Type II, the so called adult type. This type of diabetes is normally treated by diet control. For this utility, the two pronged attack of appetite suppression coupled with actual weight loss is ideal.

RESULTS

The following results were obtained with compounds of the invention utilizing the above protocol or minor modifications thereto.

TABLE I

| Compound of Example | Body weight on day 22 |
|---|---|
| 1 | 85% of control |
| 2 | 90% of control |
| 3 | 81% of control | the above results were statistically significant compared to controls (n=5-8, p≦=0.05).

PHARMACEUTICAL COMPOSITIONS

Also parts of the present invention are pharmaceutical compositions containing compounds of formula (I) in combination with a pharmaceutically acceptable diluent or carrier as well as methods for treating obesity in an obese patient or treating diabetes which involves administering such a pharmaceutical composition to the patient.

The compounds of the invention of formula (I) are useful in treating man and animals, particularly pets such as cats and dogs, and domesticated farm animals such as pigs.

The compounds of the invention of formula (I) can be administered orally, topically or parenterally, e.g. rectal or i.v., of which the preferred route is parenterally. The compounds may be admixed with conventional tableting aids, diluents, excepients as known in the art to form tablets, capsules, powders, elixirs, liquids or suspensions as known in the pharmaceutical art. For administration to humans, the compounds of the invention may be administered in an amount of about 0.1 to 1.0 mm/kg about 1-4 times per day. The particular dosage will depend on the activity of the specific compound chosen and the severity of the physiological condition being treated. The projected dosage can be determined by correlation of test results in pharmacological tests for known anti-obesity agents such as cobalt protoporphyrin and cobalt mesoporphyrin as described in PCT Patent WO 90/09173 to those for compounds of formula (I).

In more detail, the compounds of the invention will normally be administered parenterally, i.e. intravenously, subcutaneously or intramuscularly in sterile, isotonic parenteral solutions. For such solutions, any of a wide variety of pharmaceutically acceptable carriers currently in use for the preparation of parenteral solutions may be employed. The solutions may be buffered, for example with a phosphate buffer to a pH of about 7 to 8, preferably 7.4 to 7.5, and contain such solutes as saline or glucose. The solutions may also contain a polyhydroxy alcohol such as ethylene or propylene glycol. The active compounds may also be administered in solution or suspension in a sterile inert oil such as sesame or safflower oil. A typical dosage regimen for humans will be from about 0.5 to 2 mm/kg b.w. per week.

Typically, isotonic solutions for use in this invention can be prepared by dissolving the selected amount of active compound in 0.1M aqueous sodium hydroxide solution, adjusting to the selected pH with 1M hydrochloric acid, and making up to volume with 0.9 aqueous sodium chloride solution. For the low levels of active agent utilized in the practice of this invention, parenteral compositions will normally be prepared to contain from about 1 to 15 mg/ml.

The physician or veterinarian will determine the specific dosage, and it will depend upon such well understood factors as the age, weight and general health of the patient. Typically, treatment will be initiated at a dosage level of about 0.5 to 1 mm/kg b.w. and the patient will be observed so that the decline in weight is not too precipitous. Too rapid a decline in weight could elicit toxic effects similar to those observed in starvation, i.e., kidney damage, ketosis, electrolyte imbalance, etc. Therefore, the object will be to decrease weight gradually, in effect to titrate the patient so that the weight is brought under control without attendant undesirable effects.

In the following Examples and throughout the specification, the following abbreviations may be used: g (grams); ml (milliliters); hrs (hours); TLC (thin layer chromatography); > (greater than); m.p. (melting point); uv (ultraviolet); Me (methyl); THF (tetrahydrofuran); $LiAlH_4$ (lithium aluminum hydride); $CH_3SO_2Cl$ (methanesulfonyl chloride); ppm (parts per million); mmol (millimoles); py (pyridine); kg b.w. (kilograms of body weight); and mm (micromoles). Unless otherwise noted, all temperatures are in °C. (degrees Centigrade).

EXAMPLES

Example 1

2,4-Bis(2-cyanoethyl)-6,7-Bis(2-carboxyethyl)-1,3,5,8-tetramethyl cobalt porphyrin (Formula Ia)

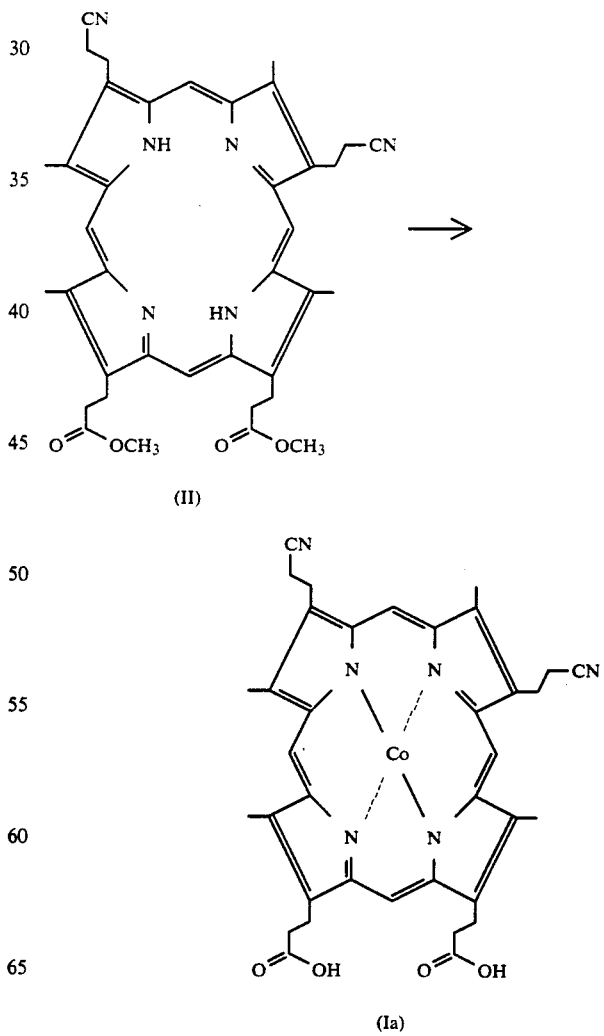

According to Kenner, G. W., et al., Liebigs Ann. Chem. 1973, 1329–1338 and Burns, D. H., et al., J. Chem. Soc., Perkin Trans. 1, 1988, 3119, to a solution of 2,4-bis(2-bromoethyl)-6,7-bis(2-methoxycarbonylethyl)-1,3,5,8-tetramethylprophyrin (500 mg, 0.654 mmol) in N-methyl-2-pyrrolidone (35 ml), the compound of formula (IIa),

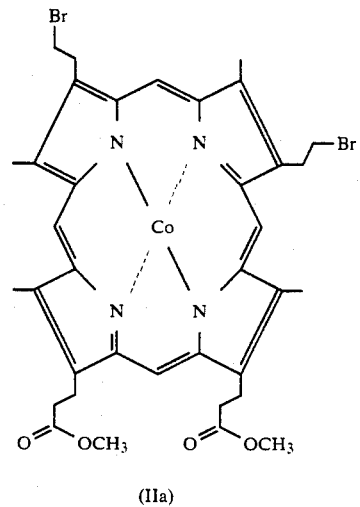

(IIa)

is added sodium cyanide (1 g) and the reaction stirred for 5 hours at 40° C. The reaction is then cooled to room temperature, dilute acetic acid (2 ml in 400 ml water) added and the mixture extracted with methylene chloride (3×100 ml). The organic layers are washed with saturated aqueous NaHCO$_3$ (1×100 ml), dried and concentrated. The concentration is dissolved in diethylether, treated with a small amount of diazomethane (to convert hydrolized acid back to methylester), concentration and chromatographed on alumina (activity V). Concentration and crystallization from methylene chloride/hexane) gave 2,4-bis(2-cyanoethyl)-6,7-bis(2-methoxycarbonylethyl)-1,3,5,8-tetramethylporphyrin, the compound of formula (II); yield: 316 mg (75%); m.p. 201°–205° C. (lit. 202°–205° C.).

To a solution of 2,4-bis(2-cyanoethyl)-6,7-bis(2-methoxycarbonylethyl)1,3,5,8-tetramethyl prophyrin of formula (II) (297 mg, 0.461 mmol) in chloroform (50 ml) is added cobalt acetate tetrahydrate (202 mg, 0.811 mmol) in methanol and refluxed for 2 hr with a drying tube attached. The solution is then filtered through silica gel and concentrated. To the resulting solid added tetrahydrofuran (50 ml), water (5 ml) and potassium hydroxide (516 mg, 9.212 mmol). The solution is refluxed overnight, neutralized with concentrated hydrochloric acid, concentrated and acidified with 10% aqueous hydrochloric acid solution to pH=1. The precipitates are collected by filtration and washed with diethyl ether and water to give the title cobalt porphyrin; yield: 282 mg, (90%); m.p. >250° C.; >98% pure by UV at 415 nm reverse-phase HPLC (C-18 column, 20:80 solvent A to B; solvent A-90:10 methanol:1M ammonium acetate; solvent B-60:40 methanol:1M ammonium acetate).

Elemental Analysis for C$_{36}$H$_{34}$N$_6$O$_4$Co·1H$_2$O: Calculated: % C, 62.52; % H, 5.25. Found: % C, 62.29; % H, 5.44.

FAB mass spectrum in meta-nitrobenzyl alcohol: m/z 673 (M+).

Example 2

Cobalt Coproporphyrin III (Formula (Ib))

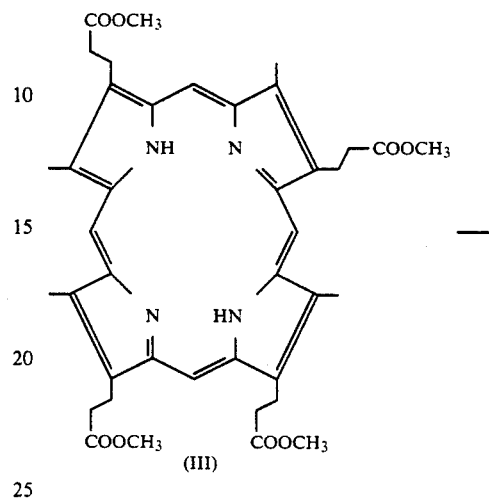

(III)

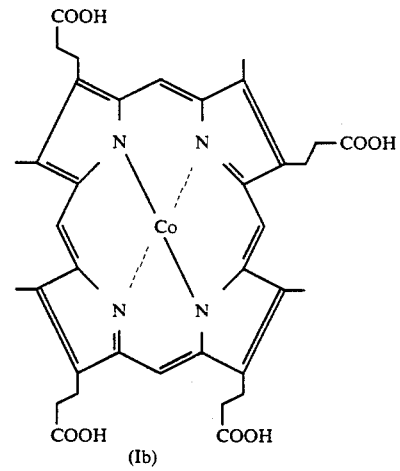

(Ib)

The procedure of Example 1 was followed except Coproporphyrin-III tetramethylester of formula (III) (prepared according to Kenner, G. W. et al., Liebigs Ann. Chem. 1973, 1329–1338) was substituted for 2,4-bis(2-cyanoethyl)-6,7-bis(2-methoxycarbonylethyl)-1,3,5,8-tetramethyl porphyrin to afford the cobalt Coproporphyrin-III; yield: 98%; m.p. >250° C.; >98% pure by UV at 415 nm reverse-phase HPLC (C-18 column, 20:80 solvent A to B; solvent A-90:10 methanol:1M ammonium acetate; solvent B-60:40 methanol:1M ammonium acetate).

Elemental Analysis for C$_{36}$H$_{36}$N$_4$O$_8$CoCl·1H$_2$O: Calculated: % C, 56.51; % H, 5.01. Found: % C, 56.51; % H, 5.08.

FAB mass spectrum in meta-nitrobenzyl alcohol: m/z 711 (M+).

Example 3

Cobalt Deuteroporphyrin IX (Formula (Ic))

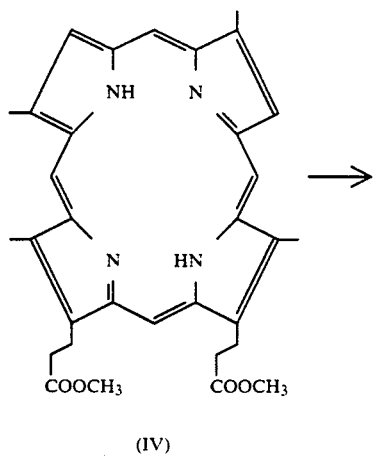

(IV)

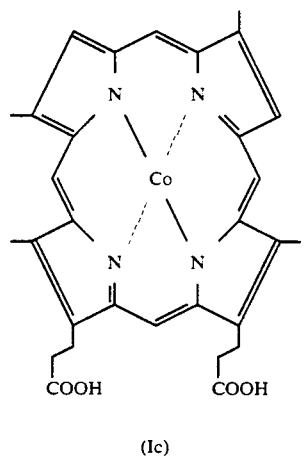

(Ic)

The procedure of Example 1 was followed except Deuteroporphyrin IX dimethylester of formula (IV) (Aldrich Chem. Co.; Milwaukee, Wis.) was substituted for 2,4-bis(2-cyanoethyl)-6,7-bis(2-methoxycarbonylethyl)-1,3,5,8-tetramethyl porphyrin to yield the cobalt Deuteroporphyrin IX of formula (Ic); yield: 74% m.p. 250° C.; >98% pure by UV at 415 nm reverse-phase HPLC (C-18 column, 70:30 methanol:1M ammonium acetate).

Elemental Analysis for $C_{30}H_{28}N_4O_4Co \cdot \frac{1}{2}H_2O$ Calculated: % C, 62.50; % H, 5.08; % N, 9.72. Found: % C, 62.10; % H, 5.07; % N, 9.61.

FAB mass spectrum in meta-nitrobenzyl alcohol: m/z 567 (M+).

Example A

The following examples illustrate pharmaceutical formulations according to the invention containing 2,4-bis(2-cyanoethyl)-6,7-bis(2-carboxyethyl)-1,3,5,8-tetramethyl cobalt porphyrin as the active ingredient. Other compounds of the invention may be formulated in a similar manner.

| TABLETS FOR ORAL ADMINISTRATION DIRECT COMPRESSION | |
|---|---|
| | mg/tablet |
| Active Ingredient | 25 |
| Calcium hydrogen phosphate B.P.* | 72.5 |
| Croscarmellose sodium USP | 2.00 |
| Magnesium Stearate. B.P. | 0.50 |
| Compression Weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | |
|---|---|
| | mg/tablet |
| Active Ingredient | 25 |
| *Starch 1500 | 174 |
| Magnesium Stearate | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | |
|---|---|
| | mg/5 ml dose |
| Active Ingredient | 25 |
| Buffer | as required |
| Flavour | as required |
| Colour | as required |
| Preservative | as required |
| Thickening Agent | as required |
| Sweetening agent | as required |
| Purified Water to | 5.00 ml |

The active ingredient, buffer, flavour, colour, preservative, thickening agent and sweetening agent are dissolved in some water, the solution is adjusted to volume and mixed. The syrup produced is clarified by filtration.

What is claimed is:

1. A cobalt porphyrin of the following formula (Ia):

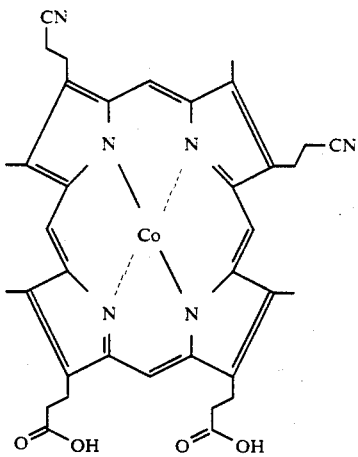

(Ia)

or a pharmaceutically acceptable salt or complex thereof with an aromatic base ligand selected from the group consisting of pyridine, imidazole, and 2-methylimidazole.

2. A pharmaceutical composition comprising a pharmaceutically effective amount of a cobalt porphyrin of the following formula (I):

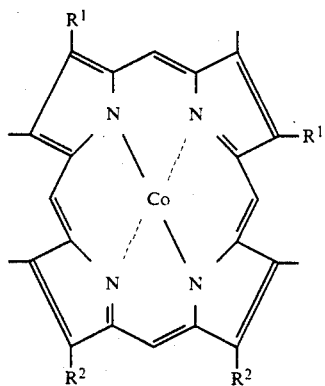

(I)

or a pharmaceutically acceptable salt or complex thereof with an aromatic base ligand selected from the group consisting of pyridine, imidazole, and 2-methylimidazole, wherein:

$R^1$ is —$CH_2CH_2CN$ and $R^2$ is —$CH_2CH_2COOH$;
$R^1$ is —$CH_2CH_2COOH$ and $R^2$ is —$CH_2C_2COOH$; or
$R^1$ is hydrogen and $R^2$ is —$CH_2CH_2COOH$,
and a pharmaceutically acceptable diluent or carrier.

3. The composition of claim 1, wherein in said cobalt porphyrin, $R^1$ is —$CH_2CH_2CN$ and $R^2$ is —$CH_2CH_2COOH$, or a pharmaceutically acceptable salt or complex thereof with an aromatic base ligand selected from the group consisting of pyridine, imidazole, and 2-methylimidazole.

4. The composition of claim 1, wherein in said cobalt porphyrin, $R^1$ is —$CH_2CH_2COOH$ and $R^2$ is —$CH_2CH_2COOH$, or a pharmaceutically acceptable salt or complex thereof with an aromatic base ligand selected from the group consisting of pyridine, imidazole, and 2-methylimidazole.

5. The composition of claim 1, wherein in said cobalt porphyrin, $R^1$ is hydrogen and $R^2$ is —$CH_2CH_2COOH$, or a pharmaceutically acceptable salt or complex thereof with an aromatic base ligand selected from the group consisting of pyridine, imidazole, and 2-methylimidazole.

6. A method for treating obesity in an obese patient or animal which comprises administering to said patient or animal, an obesity treating effective amount of the pharmaceutical composition of claim 2.

7. A method for treating obesity in an obese patient or animal which comprises administering to said patient or animal, an obesity treating effective amount of the pharmaceutical composition of claim 3.

8. A method for treating obesity in an obese patient or animal which comprises administering to said patient or animal, an obesity treating effective amount of the pharmaceutical composition of claim 4.

9. A method for treating obesity in an obese patient or animal which comprises administering to said patient or animal, an obesity treating effective amount of the pharmaceutical composition of claim 5.

* * * * *